United States Patent [19]
Spiridigliozzi et al.

[11] Patent Number: 5,824,055
[45] Date of Patent: Oct. 20, 1998

[54] STENT GRAFT DELIVERY SYSTEM AND METHODS OF USE

[75] Inventors: John Spiridigliozzi, Belmont; Amir Abolfathi, Palo Alto; Farhad Khosravi, San Mateo; Michael R. Ross, Hillsborough, all of Calif.

[73] Assignee: Endotex Interventional Systems, Inc., Menlo Park, Calif.

[21] Appl. No.: 824,012

[22] Filed: Mar. 25, 1997

[51] Int. Cl.⁶ .................................................. A61F 2/06
[52] U.S. Cl. ................................................ 623/1; 606/195
[58] Field of Search .................................. 623/1, 11, 12; 606/194, 195

[56] References Cited

U.S. PATENT DOCUMENTS

| | | | |
|---|---|---|---|
| Re. 34,327 | 7/1993 | Kreamer | 623/1 |
| 4,140,126 | 2/1979 | Choudhury | 128/325 |
| 4,503,569 | 3/1985 | Dotter | 3/1.4 |
| 4,562,596 | 1/1986 | Kornberg | 623/1 |
| 4,617,932 | 10/1986 | Kornberg | 128/343 |
| 4,733,655 | 3/1988 | Palmaz | 128/343 |
| 4,787,899 | 11/1988 | Lazarus | 623/1 |
| 5,078,726 | 1/1992 | Kreamer | 606/194 |
| 5,147,370 | 9/1992 | McNamara et al. | 606/108 |
| 5,211,658 | 5/1993 | Clouse | 623/1 |
| 5,219,355 | 6/1993 | Parodi | 606/191 |
| 5,314,444 | 5/1994 | Gianturco | 606/195 |
| 5,330,500 | 7/1994 | Song | 606/198 |
| 5,360,443 | 11/1994 | Barone et al. | 623/1 |
| 5,366,473 | 11/1994 | Winston et al. | 606/198 |
| 5,387,235 | 2/1995 | Chuter | 623/1 |
| 5,443,500 | 8/1995 | Sigwart | 623/1 |
| 5,456,713 | 10/1995 | Chuter | 623/1 |
| 5,489,295 | 2/1996 | Piplani et al. | 623/1 |
| 5,507,769 | 4/1996 | Marin et al. | 606/198 |
| 5,522,882 | 6/1996 | Gaterud et al. | 623/1 |
| 5,522,883 | 6/1996 | Slater et al. | 623/1 |
| 5,571,173 | 11/1996 | Parodi | 623/1 |
| 5,683,451 | 11/1997 | Lenker | 623/1 |

*Primary Examiner*—Michael J. Milano
*Attorney, Agent, or Firm*—Fish & Neave; Nicola A. Pisano

[57] ABSTRACT

A stent-graft delivery system and methods for use are provided for use in treating aneurysms occurring in single and bifurcated lumen hollow-body organs or vessels and for treating arterio-venous fistulas. A graft delivery component provides a clinician with complete control over the location of a graft at any time prior to implantation of stents, even when the graft is deployed from its introducer catheter. The graft delivery component includes a plurality of radially expandable fingers that releasably engage the graft, while the stent delivery component includes a small diameter introducer catheter and permits a wide range of conventional stent designs to be used to permanently fix the graft in position.

30 Claims, 10 Drawing Sheets

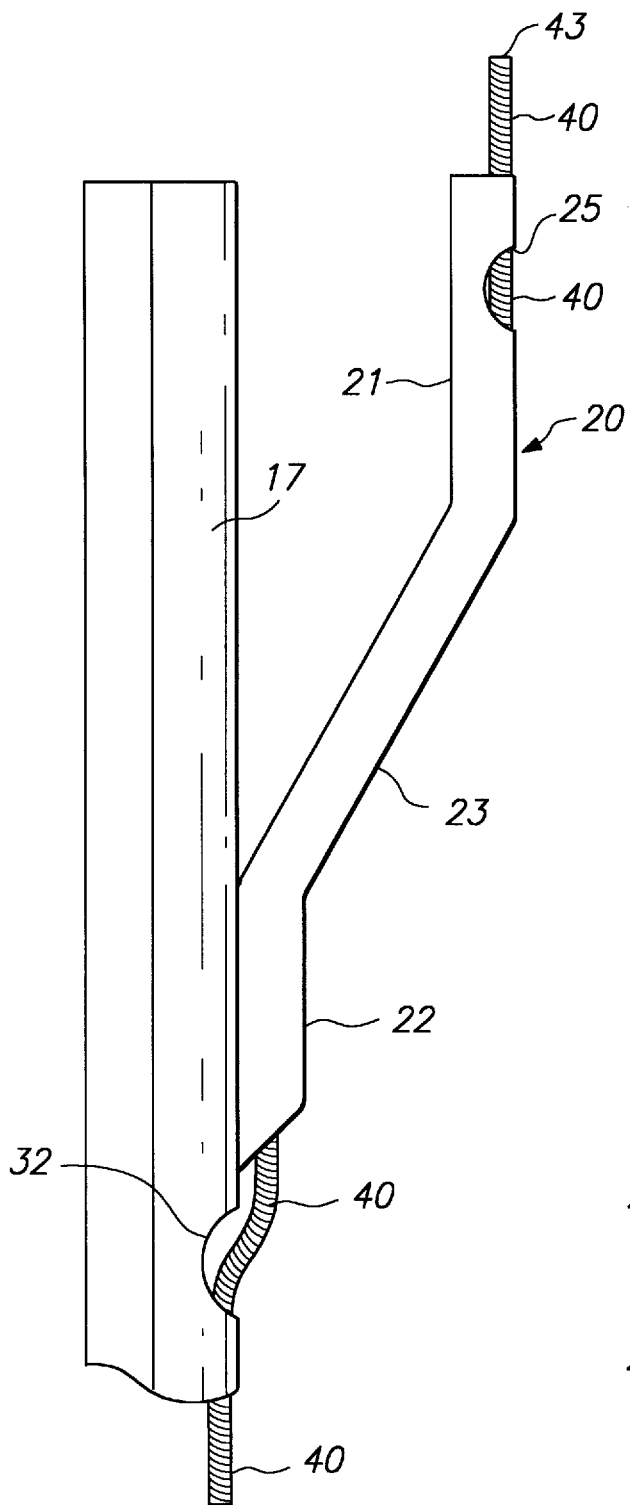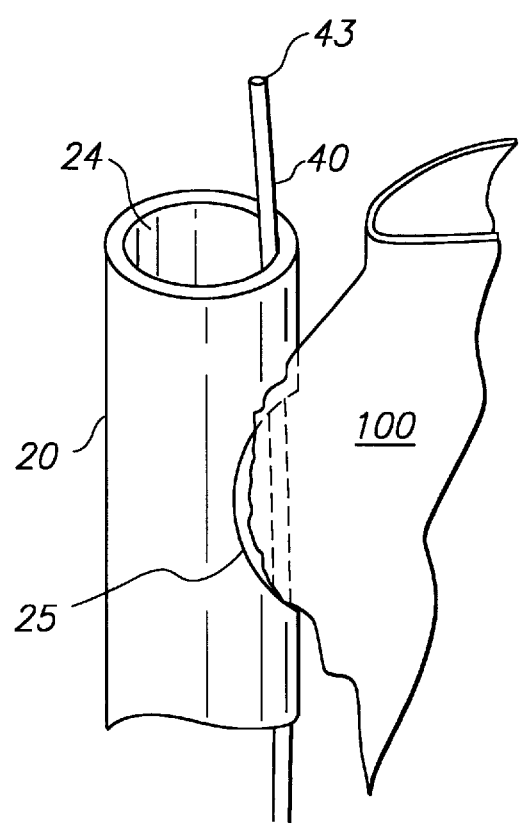
FIG. 1B
FIG. 1C

STENT GRAFT DELIVERY SYSTEM AND METHODS OF USE

FIELD OF THE INVENTION

The present invention relates generally to minimally-invasive techniques for repairing aneurysms occurring in hollow-body biological organs or vessels, for example, the abdominal aorta, and for repairing arterio-venous fistulas. More particularly, the present invention relates to methods and apparatus for repairing aneurysms and fistulas that permit adjustment and/or retrieval of a graft within a single lumen or bifurcated lumen of a hollow-body organ or vessel.

BACKGROUND OF THE INVENTION

In recent years a number of minimally-invasive techniques have been developed to repair aneurysms occurring in hollow-body biological organs or vessels, for example, the abdominal aorta, using stent-graft techniques. These techniques generally seek to "re-line" a flow path through the organ, for example, by fixing a graft across the weakened tissue of the aneurysm. The graft is then held in place with one or more stents or barbed elements, which may be implanted, for example, using a balloon catheter. Such arrangements are described, for example, in Parodi U.S. Pat. No. 5,219,355, Clouse U.S. Pat. No. 5,211,658, and Kornberg U.S. Pat. No. 4,617,932.

A drawback common to such previously known methods and apparatus, especially those such as the Parodi and Clouse patents, is the inability to adjust or retrieve the graft once it has been deployed from an introducer catheter. Generally, deployment of the graft (or the stent in Clouse system) marks a point of no-return—if the graft is determined to be in an inappropriate position, or the graft size is inadequate, it is not possible to abort the procedure.

Thus, previously known methods and apparatus cannot, for example, adjust the placement of the graft relative to the portions of the organ or vessel proximal and distal to the aneurysm (i.e., the proximal neck and the distal cuff of the aneurysm) once the graft is deployed. Neither can such methods and apparatus correct for migration of the graft between the time of its deployment and when the graft is affixed to the organ or vessel walls via stents, etc. See, for example, the catalog of complications resulting from mispositioning and/or migration described in T. Chuter et al. in *Endoluminal Vascular Prostheses*, Little Brown & Co. (1995), Chapter 3 at page 50.

Another drawback of previously known stent-graft systems, for example, those systems having integrated grafts and stents, is that large diameter introducer catheters are needed to deliver such systems. A typical previously known stent-graft system may include a central delivery shaft having a diameter of 1.5–1.75 mm, a deployment balloon having a thickness of 0.5–0.75 mm, an anchoring stent with a thickness of 0.3–0.6 mm, a synthetic graft with a thickness of 0.25–0.5 mm, and a delivery sheath having a thickness of 0.5–0.75 mm. The stacking of these thicknesses results in a combined thickness of 4–7 mm, which must be inserted through a vascular system generally having a diameter in a range of 5–7 mm.

Not surprisingly, the large-diameter introducer catheters needed for such previously known stent-graft systems, for example, 22–26 French, create problems in delivering such systems transluminally via the femoral arteries. In particular, the thicker diameters reduce the clinician's ability to maneuver the stent-graft system into position along a tortuous path. See, for example, Chapter 3 of the foregoing text at pp. 40–41, 44 and 48, which describes spasm and delivery problems associated with the use of large introducer catheters employed with previously known stent-graft delivery systems.

In view of the foregoing, it would be desirable to provide a stent-graft delivery system and methods for use for repairing aneurysms and fistulas, that enable the graft position to be adjusted after the graft has been deployed from an introducer catheter.

It further would be desirable to provide a stent-graft delivery system and methods for use for repairing aneurysms that enable the use of much smaller diameter introducer catheters than can be used with previously known stent-graft delivery systems, thereby reducing problems associated with the use of large diameter introducer catheters.

It also would be desirable to provide a stent-graft delivery system and methods for use for repairing aneurysms that enable a graft to be retrieved and withdrawn from the patient's body after partial deployment, for example, to be exchanged for a graft of a different size.

It further would be desirable to provide a stent-graft delivery system and methods for use for repairing aneurysms that enable a graft to be positioned with equal ease in either single lumen or bifurcated lumen organs and vessels, to permit treatment of a large range of aneurysms and other defects.

SUMMARY OF THE INVENTION

In view of the foregoing, it is an object of this invention to provide a stent-graft delivery system and methods for use for repairing aneurysms and fistulas, that enable the graft position to be adjusted after the graft has been deployed from an introducer catheter.

It is a further object of the present invention to provide a stent-graft delivery system for repairing aneurysms and fistulas that enable the use of much smaller diameter introducer catheters than used with previously known stent-graft systems, thereby reducing problems associated with the use of large diameter introducer catheters.

It is another object of this invention to provide stent-graft delivery systems suitable for excluding aneurysms in hollow-body organs and vessels other than the aorta, for example, in gastro-intestinal, respiratory, reproductive organ and urethral applications and elsewhere where is desirable to "reline" a hollow-body organ or vessel, and for use in treating arterio-venous fistulas.

It is yet another object of this invention to provide stent-graft delivery systems for repairing aneurysms and fistulas that enable a graft to be entirely retrieved after deployment from an introducer catheter, for example, to be exchanged for a graft of a different size.

It is a further object of the invention to provide a stent-graft delivery system and methods for use for repairing aneurysms that enable a graft to be positioned and in either single lumen or bifurcated lumen organs and vessels, to permit treatment of a large range of aneurysms and other defects.

These and other objects of the invention are accomplished in accordance with the principles of the invention by providing stent-graft delivery systems that provide the clinician with complete control over the location of the graft, even after the graft is deployed from an introducer catheter. Thus, if a graft is determined to be mispositioned, the clinician may adjust the graft, or if the size is thought to be inappropriate, the clinician may withdraw the graft and substitute a graft of a different size.

In accordance with the invention, the graft and stent delivery components of a stent-graft system are separately delivered transluminally to the site of an aneurysm using small diameter catheters (e.g., 12–16 French for the graft, about 9–10 French for the stent). The graft component is releasably engaged with a plurality of radially expandable fingers that permit the location of the graft to be freely manipulated by the clinician after deployment from an introducer catheter.

The radially expandable fingers of the graft delivery component permit the graft to be held in position while stents are deployed to permanently fasten the graft in place, and also enable the graft to be fully retracted into its associated introducer catheter after deployment. A stent delivery component of the system is also inserted transluminally to the site of the aneurysm via a small diameter introducer catheter, and permits use of a wide range of conventional stent designs to permanently fix the graft in position.

Methods and apparatus for using a stent-graft system constructed in accordance with the principles of the present invention for repairing aneurysms and other defects in single and bifurcated body lumens are also provided.

BRIEF DESCRIPTION OF THE DRAWINGS

Further features of the invention, its nature and various advantages will be more apparent from the accompanying drawings and the following detailed description of the preferred embodiments, in which:

FIGS. 1A, 1B and 1C are, respectively, illustrative views of the graft delivery component of a stent-graft delivery system constructed in accordance with the present invention;

DETAILED DESCRIPTION OF THE INVENTION

The present invention provides apparatus and methods for the treatment of aneurysms occurring in single lumen and bifurcated lumen hollow-body organs and vessels, and for the treatment of arterio-venous fistulas, that overcome certain limitations of previously known stent-graft systems. In particular, the apparatus and methods of the present invention enable a clinician to adjust the positioning of a graft after it has been deployed from its associated introducer catheter, and even enable the clinician to retrieve the graft should it be determined that a graft of a different size is required.

The following description first describes the stent and graft delivery components of the present invention in the context of treating single lumen hollow-body organs and vessels; the description next describes certain auxiliary devices for use in conjunction with the stent-graft delivery system of the present invention for treating bifurcated lumens of hollow-body organs and vessels.

Figure 1A:
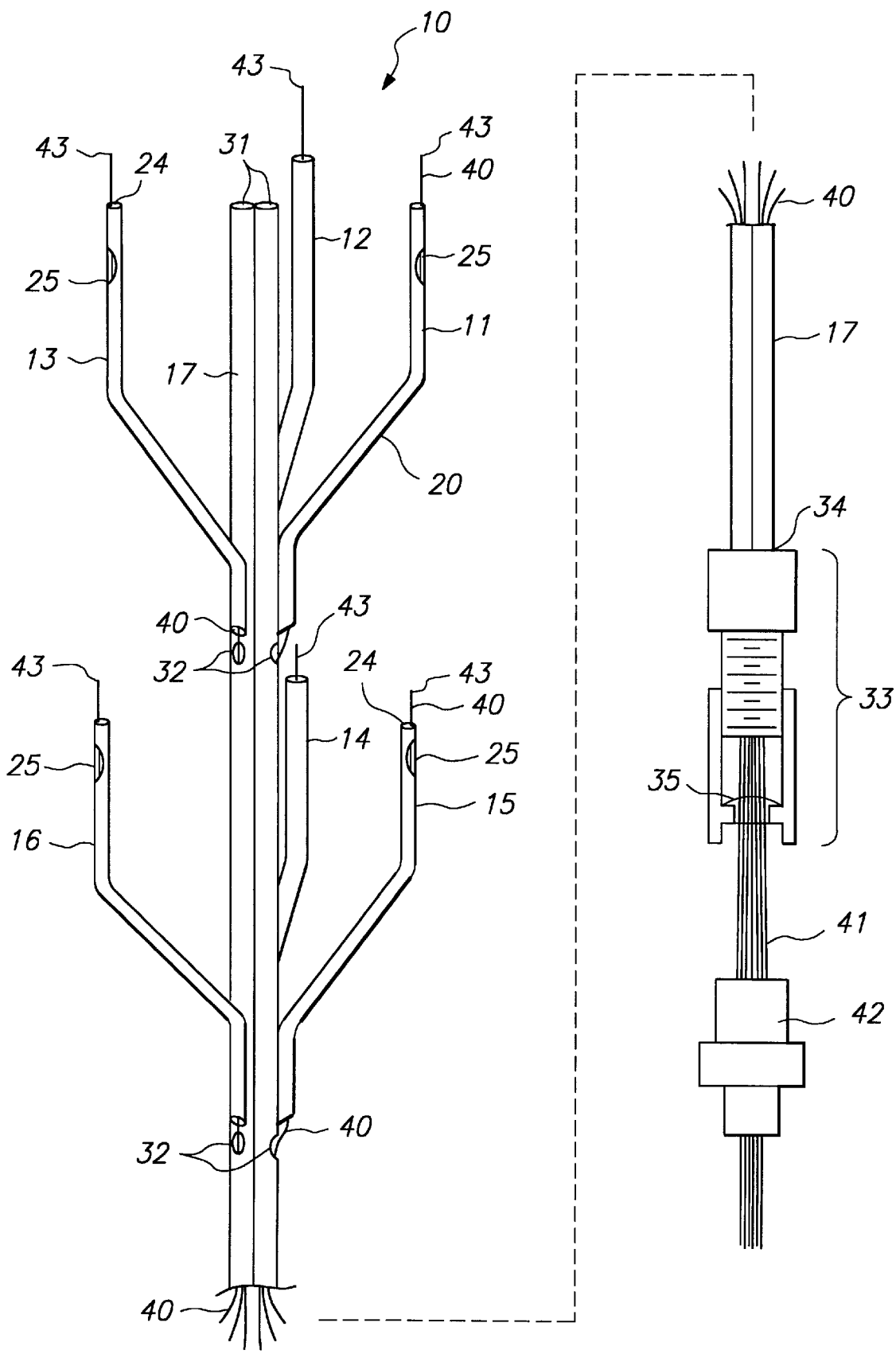

Referring to FIGS. 1A through 1C, graft delivery component 10 constructed in accordance with the principles of the present invention is described. Graft delivery component 10 is designed to releasably and adjustably grasp a synthetic tubular graft. The graft is preferably formed from a polyester fabric, such as DACRON®, a registered trademark of the E.I. duPont de Nemours Company, Wilmington, or other biocompatible material, such as PTFE (polytetrafluoroethylene). Graft delivery component 10 comprises a plurality of radially outwardly expanding fingers arranged in a distal group of fingers 11, 12 and 13 and a proximal group of fingers 14, 15 and 16. Fingers 11–16 are fastened to support tube 17, with the fingers in each group spaced equidistant apart around the circumference of support tube 17.

Throughout this specification, proximal is used to refer to the portion of the stent-graft delivery system that extends outside the patient's body and is manipulated by the clinician, while distal refers to the end of the stent-graft delivery system disposed within a patient's body and is furthest-most from the proximal end.

Each of fingers 11–16 comprises an elastic and resilient material that expands to a deployed position, shown in FIG. 1A, when an outer sheath (see FIG. 4A) is retracted. As shown in FIGS. 1B and 1C, each of fingers 11–16 is formed from tubular element 20 to have first and second regions 21 and 22 parallel to support tube 17 (when deployed) and angled region 23 joining first and second regions 21 and 22. Each of fingers 11–16 also includes interior lumen 24 and aperture 25, disposed near the distal end of the finger, that communicates with interior lumen 24. Fingers 11–16 are affixed to support tube 17, for example, by an adhesive, welding or other suitable means, such as fasteners, such as rivets or screws.

Support tube 17 comprises one or more hollow tubular members 30 having sufficient strength to permit axial force transmission, and sufficient flexibility to negotiate tortuous curves during transluminal insertion. Support tube 17 includes one or more lumens 31 having apertures 32 disposed adjacent the proximal ends of fingers 11–16. Apertures 32 are in communication with lumen 31. Support tube 17 is sufficiently long to enable transluminal delivery (e.g., 48 inches), and includes handle 33 disposed from proximal end 34. Handle 33 is fastened to proximal end 34 of support tube 17 using a suitable fastener or potting material, and enables manipulation of support tube 17. Support tube 17 may also include a lumen for accepting a conventional guidewire, thus assisting in transluminal placement of graft delivery component 10.

Retention wires 40 extend from the proximal end of graft delivery component 10 through lumen 31, and exit support tube 17 through apertures 32. Each of retention wires 40 is then routed into a proximal end of a respective finger 11–16, and extend through lumen 24 in the respective fingers to a point distal of apertures 25. Proximal ends 41 of retention wires 40 are disposed in release knob 42, so that distal ends 43 of retention wires 40 may be withdrawn in fingers 11–16 to a position proximal of apertures 25. Retention wires 40 preferably comprise a strong yet flexible biocompatible material, such as plastic or metal alloy strands.

Handle 33 preferably comprises a hemostatic valve including seal 35, through which retention wires 40 are slidably disposed. Release knob 42 includes means for gripping retention wires 40, so that a proximal force exerted on release knob 42 causes retention wires 40 to be drawn in a proximal direction.

Referring now to FIG. 1C, engagement of a tubular graft with graft delivery component 10 is described. Distal group of fingers 11–13 are engaged to tubular graft 100 near the distal end of the graft as follows. First, retention wires 40 are retracted to a position in lumens 24 proximal of apertures 25. A portion of the graft is inserted into each of apertures 25, and retention wires 40 are then extended so that distal ends 43 pierce the graft material. By further extending retention wires 40, so that distal ends 43 are disposed distally of apertures 25, the graft material becomes pinned to the respective fingers 11–16 until retention wires 40 are subsequently retracted proximally.

Figure 4A:
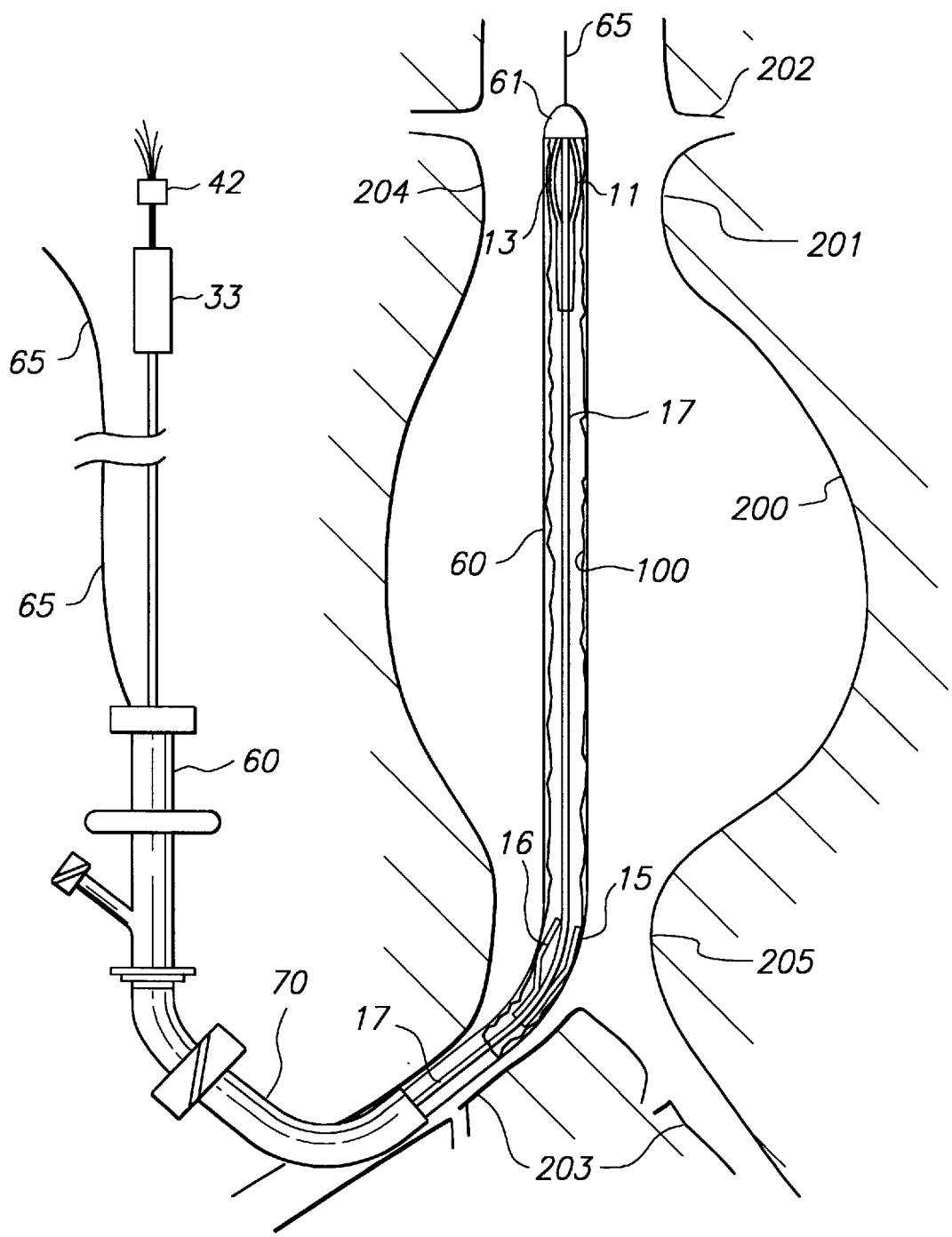
FIGS. 4A, 4B and 4C, are, respectively, elevation views, partly in section, showing positioning of a graft in an abdominal aortic aneurysm, deployment of the graft and introduction of the stent delivery component, and the appearance of the graft as permanently implanted in the aorta.

As seen in FIG. 4A, the graft and graft delivery component 10 are contracted to a reduced delivery diameter by extending an introducer catheter over the graft and graft delivery component. The introducer catheter biases the tips of radially expandable fingers 11–16 inward against the spring force created by angled portions 23 of the fingers, so that the tips are disposed adjacent one another and support tube 17. When the introducer catheter is retracted, fingers 11–16 move outwardly to open the graft approximately to its deployed diameter.

In a preferred embodiment, support tube 17 is formed of two stainless steel hypotubes having internal diameters of 0.020 inches and external diameters of 0.028 inches. The tubes are welded together side-by-side and have an overall length of about 46 inches. Fingers 11–16 are formed from 316L grade stainless steel hypotube material having an outer diameter of 0.025 inches, an interior diameter of 0.017 inches, and a length (relative to the longitudinal axis of support tube 17) of 1.5 inches. Distal group of fingers 11–13 have their distal ends approximately even with the distal end of support tube 17, while in a preferred embodiment for use in the abdominal aorta, proximal group of fingers 14–16 are positioned about 5.0 inches proximal of the distal end of the support tube. Retention wires 40 preferably are formed of nickel-titanium wires having a diameter of 0.005 inches, with an austenite transition temperature $A_f$ of about 6 degrees Celsius.

Figure 2A:
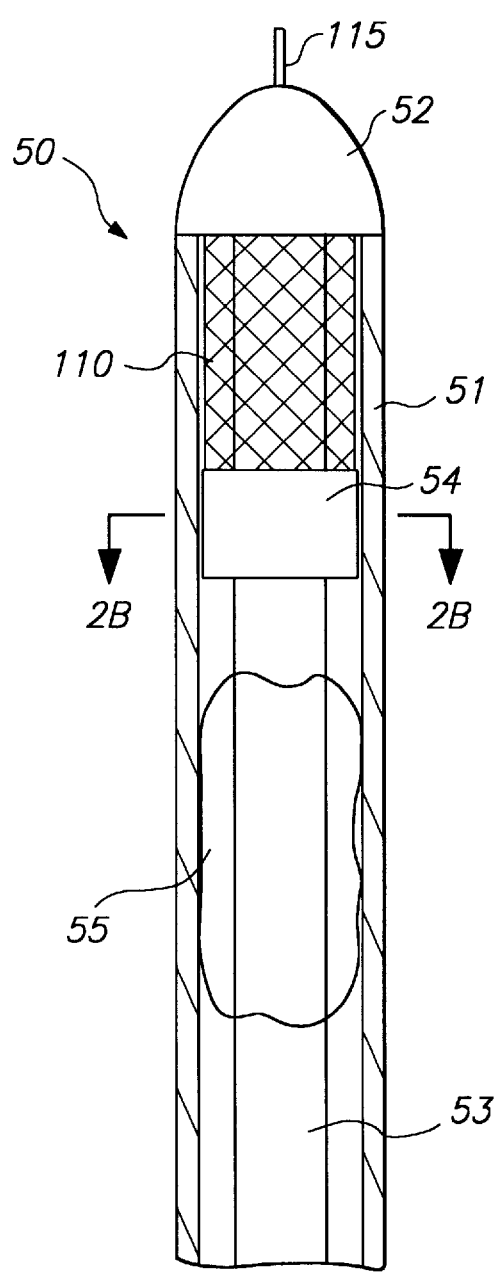
FIGS. 2A and 2B are, respectively, a partial sectional side view and a cross-sectional view along view line 2B—2B of FIG. 2A of an illustrative stent delivery component of the stent-graft system.
Figure 2B:
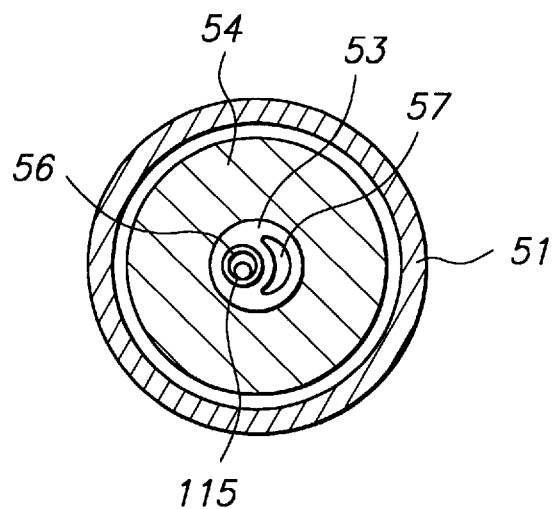
Figure 3:
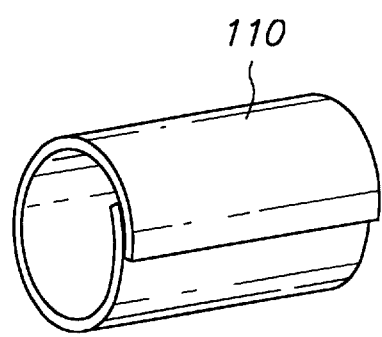
FIG. 3 is a perspective view of a stent suitable for use with the stent delivery component of FIGS. 2.

Referring now to FIGS. 2A, 2B and 3, the stent delivery component of the stent-graft delivery system of the present invention is described. Graft delivery component 10 of FIGS. 1 may be advantageously used with any of a variety of stents to cause fixation of graft 100 to the walls of an aorta. For example, the stent may comprise an elastically balloon-expanded coiled sheet, as described, for example in Kreamer U.S. Pat. No. Re. 34,327 and Sigwart U.S. Pat. No. 5,443,500 (depicted in FIG. 3); a plastically balloon-deformable wire mesh, as described for example, in Palmaz U.S. Pat. No. 4,733,665 and Gianturco U.S. Pat. No. 5,314,444; a thermally activated stent as described in Dotter U.S. Pat. No. 4,503,569; or an elastically self-expanding stent as described in McNamara U.S. Pat. No. 5,147,370, the disclosures of which are incorporated herein by reference. Stents suitable for use with the stent delivery component of the present invention preferably employ an introducer catheter (i.e., outer sheath) having a diameter of about 9–10 French.

In FIG. 2A, stent delivery component 50 includes outer sheath 51, nose cone 52, core member 53, retaining member 54 and balloon 55. Illustratively, coiled sheet stent 110 (illustrated without mesh detail in FIG. 3), of the type described in U.S. Pat. No. 5,443,550, is disposed within outer sheath 51 between nose cone 52 and retaining member 54. As shown in FIG. 2B, core member 53 includes guidewire lumen 56 and inflation lumen 57 that communicates with the interior of balloon 55. Guidewire 115 may be inserted through guidewire lumen 56 to assist in positioning the stent delivery component within the graft.

As will be apparent to one of skill in the art, coiled sheet stent 110 is wound to a contracted diameter and disposed within outer sheath 51 and about core member 53. Outer sheath 51 retains coiled sheet stent 110 in its contracted diameter. When stent delivery component 50 is positioned at the site where the stent is to be deployed, outer sheath 51 is retracted proximally. As outer sheath 51 is retracted, retaining member 54 prevents proximal movement of stent 110. When outer sheath 51 clears the proximal end of the stent, the stent expands radially outward into contact with the interior of the graft and wall of the body organ. Next, balloon 55 is advanced distally so that it is positioned within stent 110. Balloon 55 is then inflated to lock the stent at a desired expanded diameter. The balloon is then deflated and the stent delivery component is withdrawn from the patient's body.

As will be apparent to one of skill in the art, the position of balloon 55 may be moved relative to stent 110, with balloon 55 placed more proximally on core member 53 (i.e., with the relative positions shown in FIG. 2A reversed). In this case, stent 110 is deployed by retracting outer sheath 51, and then withdrawing core member 51 in a proximal position to dispose balloon 55 within the stent to lock the latter in place.

Figure 4B:
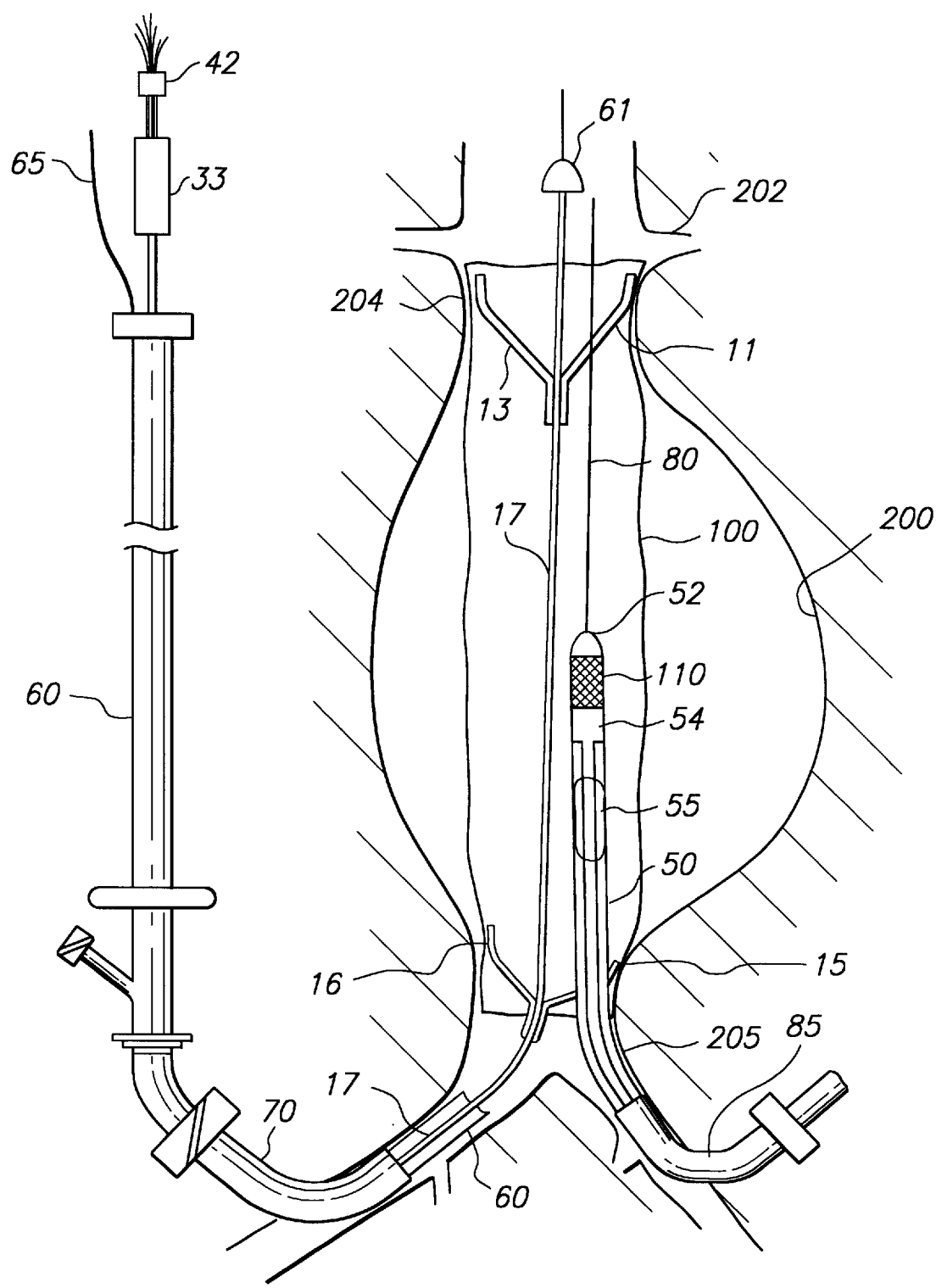
Figure 4C:
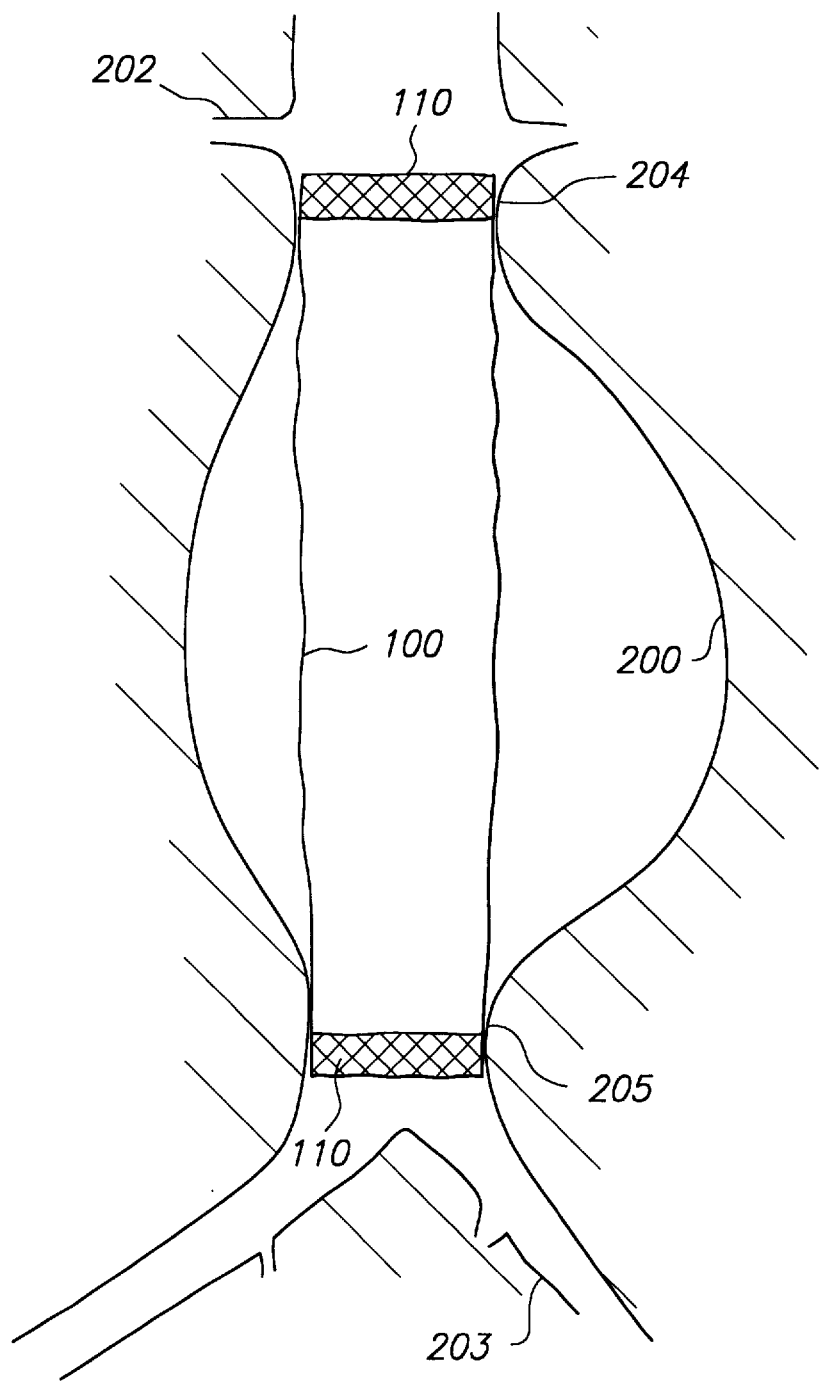

Referring now to FIGS. 4A–4C, a method of implanting single lumen graft 110 within abdominal aorta aneurysm 200 using the stent-graft system of the present invention is described.

As illustratively shown in FIG. 4A, graft 100 is engaged to graft delivery component 10 and folded within introducer catheter 60, so that fingers 11–16 are collapsed alongside support tube 17 against the inherent outward bias of the fingers. Graft delivery component 10 and introducer catheter 60 are disposed across aneurysm 200 in aorta 201 on guidewire 65 at a position located between renal arteries 202 and iliac arteries 203. Aneurysm 200 includes nondilated region of aorta 204 above the aneurysm (referred to as the "proximal neck") and distal region 205 just above the bifurcation for iliac arteries 203 (referred to as the "distal cuff").

Graft delivery component 10 and introducer catheter 60 are threaded through a femoral artery via introducer sheath 70 along guidewire 65, so that graft 100 is positioned across aneurysm 200. Nose cone 61 is disposed on a distal end of support tube 17 to facilitate insertion. In accordance with the present invention, graft delivery component 10 permits introducer catheter 60 to have a smaller diameter, for example 12–16 French, than previously known apparatus, that generally use diameters greater than 21 French. The position of introducer catheter 60 within aneurysm 200 may be determined using standard fluoroscopic techniques and a suitable high contrast agent on or radiopaque marker introducer catheter 60 or graft 100.

In FIG. 4B, graft 100 is shown fully deployed from introducer catheter 60 (which has been retracted proximally). When introducer catheter 60 is retracted in the proximal direction, fingers 11–16 (fingers 12 and 14 not visible in FIG. 4B) expand radially outward, thereby unfurling graft 100 approximately to its deployed diameter. In particular, fingers 11–16 urge graft 100 into engagement with nondilated walls 204 and 205 of the aorta. Support tube 17 of graft delivery component 10 then may be moved proximally or distally using handle 33 to maneuver graft 100 to a desired location across aneurysm 200, for example, under fluoroscopic guidance.

Once graft 100 has been moved to a desired position within aneurysm 200, stent delivery component 50 containing stent 110 in its contracted state is inserted along guidewire 80 via introducer sheath 85, so that the stent is positioned overlapping an end of graft 100. At any point prior to implantation of stent 110, the position of graft 100 may be adjusted, or the graft may be entirely withdrawn.

Referring now to FIG. 4C, graft 100 of FIG. 4B is shown affixed to the walls of aorta 201 by stents 110. Stents 110 are serially positioned and expanded into apposition with graft 100 and the walls of aorta 204 and 205 using stent delivery component 50 described above with respect to FIGS. 2A and 2B, while fingers 11–16 of graft delivery component 10 hold graft 100 in position. Once stents 110 are implanted to affix graft 100 to the walls of aorta 201, release knob 42 (see FIG. 4B) is pulled proximally to retract retention wires 40, thereby releasing graft 100 from engagement with fingers 11–16. Graft delivery component 10 is then withdrawn from the patient's body.

Whereas with previously known graft delivery systems, partial deployment of the graft (as in FIG. 2B) would terminate the clinician's ability to adjust or retrieve the graft member, in accordance with the present invention, graft 100 remains coupled to graft delivery component 10 until retention wires 40 are retracted. Thus, even though graft 100 is fully deployed from introducer catheter, its position may be adjusted within the aneurysm, by pulling (or pushing) support tube 17 in the proximal or distal directions. In addition, should the clinician determine that graft 100 is of inappropriate size, or should the clinician wish to abort the procedure, graft 100 may be completely recovered within introducer catheter 60 by extending catheter 60 in the distal direction.

In the illustrative method described above with respect to FIGS. 4A–4C, graft delivery component 10 is introduced through one of the femoral arteries, while stent delivery component 50 is introduced through the contralateral femoral artery. Alternatively, the stent delivery component may be introduced through the same femoral artery as the graft delivery component. Moreover, because the individual components of the stent-graft system of the present invention have substantially smaller diameters than previously known devices, the components may be introduced through other than the femoral arteries. For example, graft delivery component 10 and introducer catheter 60 may be introduced into the aorta via the brachial artery, while the stents may be delivered to the respective ends of graft 100 through either a femoral artery or from above via the brachial/carotid arteries.

Referring now to FIGS. 5–7, additional apparatus, constructed in accordance with the principles of the present invention, is described for use in implanting a bifurcated graft. Use of these devices in accordance with the methods of the present invention are illustrated with respect to FIGS. 8–10.

Figure 5A:
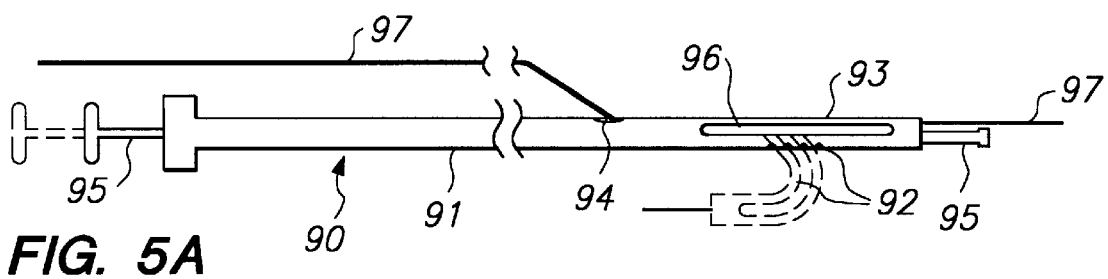
FIGS. 5A and 5B are side and end views, respectively, of a steerable guide catheter for positioning a guidewire across a bifurcation.
Figure 5B:
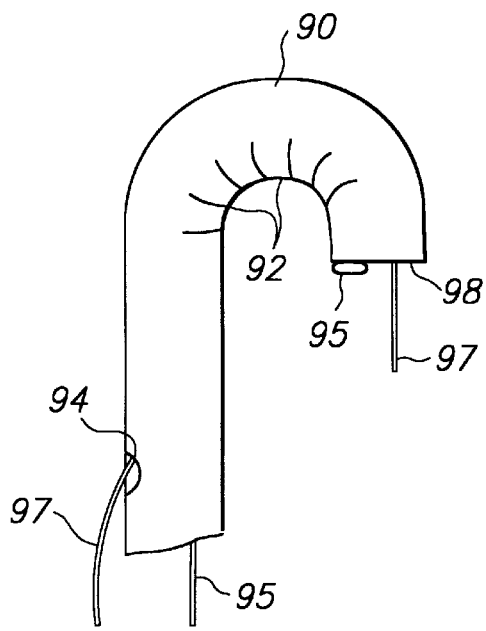

With respect to FIGS. 5A and 5B, steerable guide catheter 90 comprises small diameter catheter 91 having two internal lumens (not visible), series of notches 92 in distal end 93, and skive 94. Notches 92 extend about half of the circumference of the guide catheter, so that wire 95 disposed in one of the internal lumens causes guide catheter 90 to bend in the direction of the notches when wire 95 is retracted proximally (shown in dotted line in FIG. 5A).

Guide catheter 90 may also include a radiopaque marker band 96, visible in a fluoroscopic image, that indicates the amount of bend introduced to the tip of the guide catheter. Guidewire 97 is inserted into guide catheter 90 through skive 94 (in a rapid exchange mode) and exits guide catheter 90 through the distal end face 98 of the guide catheter. As shown in FIG. 5B, guide catheter 90 enables a clinician to change the direction of guidewire 97 a desired amount by selectively retracting wire 95 to bend distal end 93.

Figure 6A:
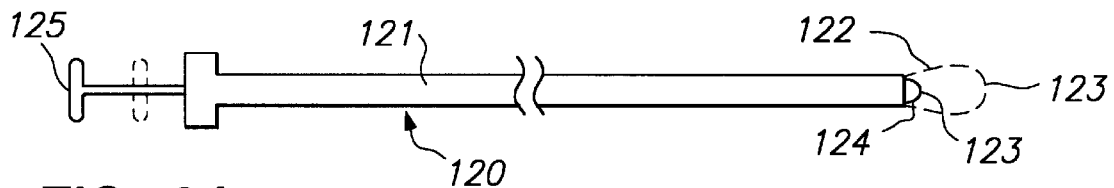
FIGS. 6A and 6B are side and end views, respectively, of a snare catheter suitable for use in practicing the methods of the present invention.
Figure 6B:
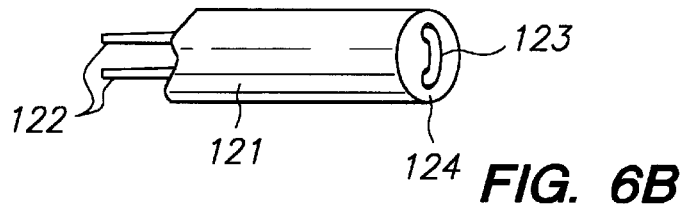

With respect to FIGS. 6A and 6B, snare catheter 120 is described. Snare catheter 120 comprises multi-lumen catheter 121 having the ends of wire 122 disposed through two of the lumens to form snare loop 123 at distal end 124 of the catheter. Wire 122 is coupled to handle 125 for reciprocation between a first position where the snare loop is extended and open (shown in dotted line in FIG. 6A) and a second position where snare loop 123 is engaged against distal end 124 of the catheter (shown in solid line in FIG. 6A). As will be apparent, handle 125 may be pushed distally to open snare loop 123 to capture an end of a guidewire, and handle 125 is then pulled proximally to engage and retain the guidewire within snare loop 123.

Figure 7A:
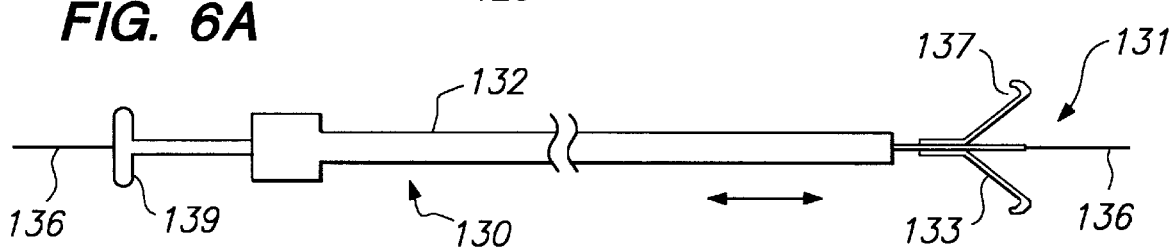
FIGS. 7A and 7B are side and end views, respectively, of a multi-finger element constructed in accordance with the present invention for positioning a side leg of a bifurcated graft.
Figure 7B:
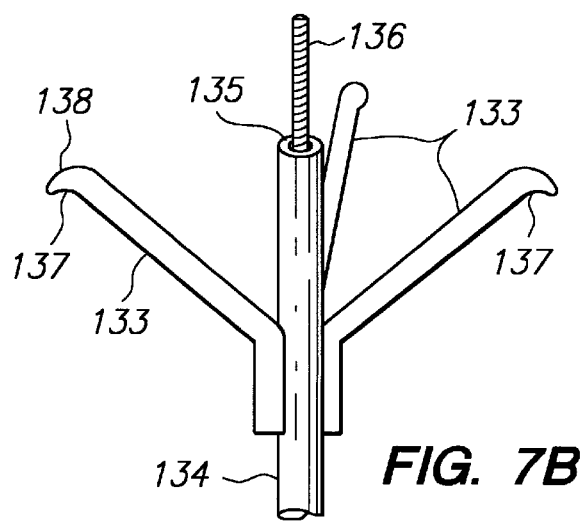

Referring to FIGS. 7A and 7B, positioning catheter 130 is described. Positioning catheter 130 comprises a multi-finger element 131 slidably disposed within a lumen of sheath 132. Multi-finger element 131 includes a plurality of resiliently radially expanding and outwardly biased fingers 133 located around the circumference of support tube 134, and central channel 135 for accepting guidewire 136 therethrough. Multi-finger element 131 is similar in construction to graft delivery component 10, except that fingers 133 do not include apertures 25 or retention wires 40. Instead, each of fingers 133 includes hook 137 disposed at tip 138 for engaging a side leg of a bifurcated graft. Multi-finger element 131 is disposed within sheath 132 so that by imparting relative motion between handle 139 and sheath 132, sheath 132 may be moved from a distal position wherein tips 138 of fingers 133 are retracted to a transit position adjacent to support tube 134, and a retracted position in which the end of sheath 132 is moved proximally of fingers 133, so that fingers 133 are deployed outwardly.

Figure 8A:
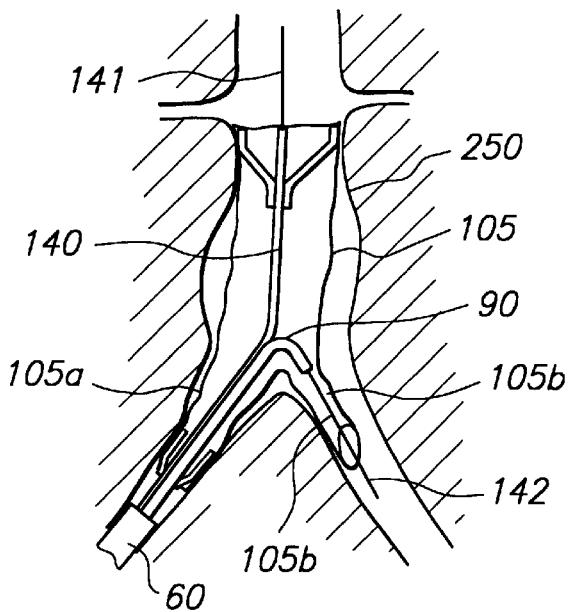
FIGS. 8A–8C and 8D are, respectively, partial sectional views showing deployment of a bifurcated graft in accordance with a first method of the present invention, and a detailed view of engagement of the multi-finger element of FIG. 7B with a side leg of the bifurcated graft.

Referring now to FIGS. 8A to 8D, a first method of deploying bifurcated graft 105 in aortic aneurysm 250 in accordance with the present invention is described. In FIG. 8A, graft delivery component 140 disposed on guidewire 141 is shown holding bifurcated graft 105 in position within aneurysm 250. Graft delivery component 140 is similar in design to the apparatus of FIG. 1, except that the proximal group of fingers is set further apart from the distal group of fingers and are located in leg 105a of bifurcated graft 105.

Consequently, when introducer catheter 60 is retracted proximally, the proximal group of fingers expand leg 105a of bifurcated graft 105 into contact with the walls of the iliac artery, rather than distal cuff 205 of the aneurysm (see FIG. 4B). Thus, FIG. 8A illustrates a step similar to that shown in FIG. 4B, where the graft has been expanded into contact with the walls of the vessel by withdrawing the introducer catheter.

Still referring to FIG. 8A, in accordance with the present invention, guide catheter 90 is advanced along guidewire 142 (through introducer catheter 60) so that distal end 93 is disposed above the iliac bifurcation. Wire 94 of guide catheter 90 is then retracted to direct guidewire 142 into the contralateral iliac artery. Guidewire 142 is then advanced so that it extends through the opening in leg 105b of graft 105 and into the contralateral iliac artery.

Figure 8B:
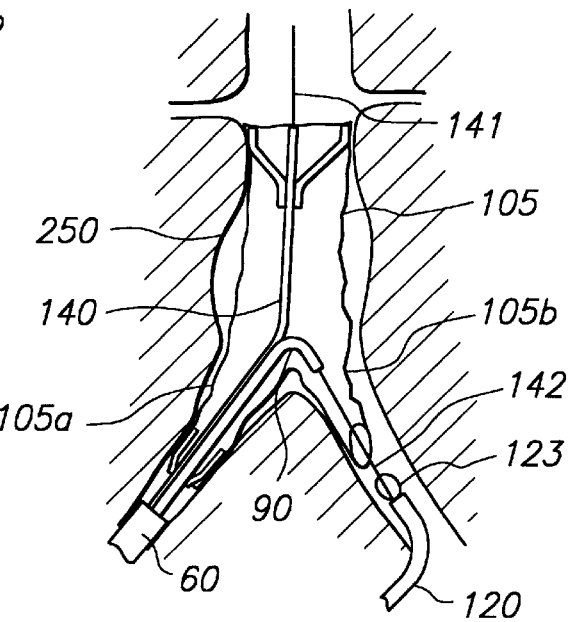

As seen in FIG. 8B, snare catheter 120 is inserted through the femoral artery and into the contralateral iliac artery. Snare catheter 120 is then manipulated, so that the end of guidewire 142 is disposed through snare loop 123, and snare loop 123 is closed to capture guidewire 142. Snare catheter 120 and guidewire 142 are then withdrawn through the opening in the contralateral iliac artery. Guide catheter 90 is also withdrawn, leaving guidewire 142 extending across the iliac bifurcation.

Figure 8C:
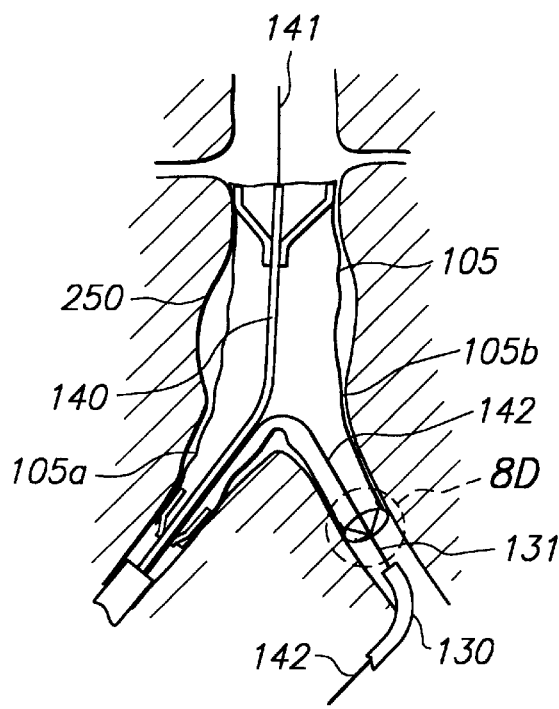
Figure 8D:
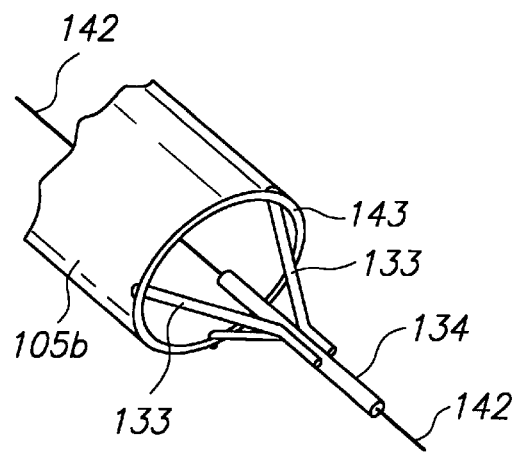

With respect to FIG. 8C, positioning catheter 130 is advanced along guidewire 142 through the contralateral iliac artery until multi-finger element 131 is disposed within leg 105b of graft 105. Sheath 132 of positioning catheter 130 is withdrawn and fingers 133 move outwardly to engage and expand leg 105b (shown in detail in FIG. 8D). Next, positioning catheter 130 is pulled proximally to pull leg 105b of graft 105 into the iliac artery and hold it taut while it is affixed to the artery wall. Leg 105b may include a biocompatible elastic ring 143 that is engaged by hooks 137 of multi-finger element 131, to assist in pulling leg 105b into position in the contralateral iliac artery.

A stent delivery component, as described above with respect to FIGS. 2, is then positioned in leg 105b, either from above through the brachial/carotid arteries, or from below through the femoral artery, to fasten leg 105b in place. Multi-finger element 131, like graft delivery component 10, enables a stent to be deployed to fasten the leg of the graft in place while it is held in position by the multi-finger element. Stents are also placed in leg 105a of the graft and in the region of the graft in the proximal cuff. Multi-finger element 131 is then moved slightly distally to disengage hooks 137 from graft 105 and sheath 132 is moved to its distal position to retract fingers 133 to the transit position. Positioning catheter 130 and guidewire 142 are then removed.

Figure 9A:
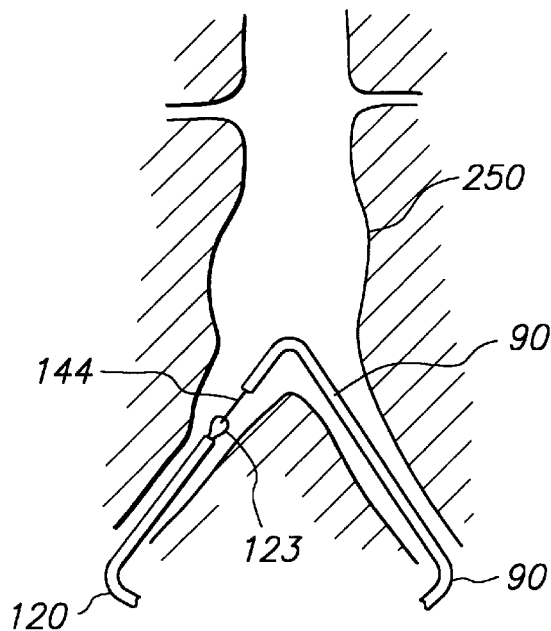
FIGS. 9A–9C are partial sectional views showing deployment of a bifurcated graft in accordance with another method of the present invention.
Figure 9B:
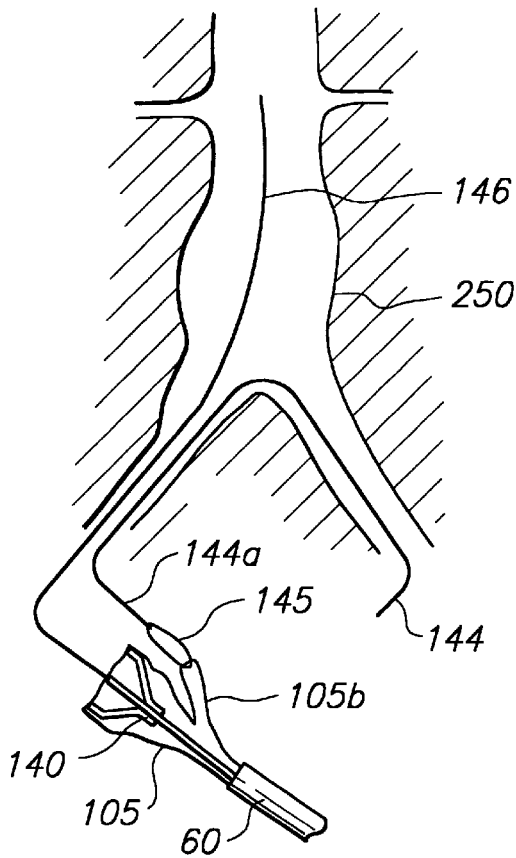
Figure 9C:
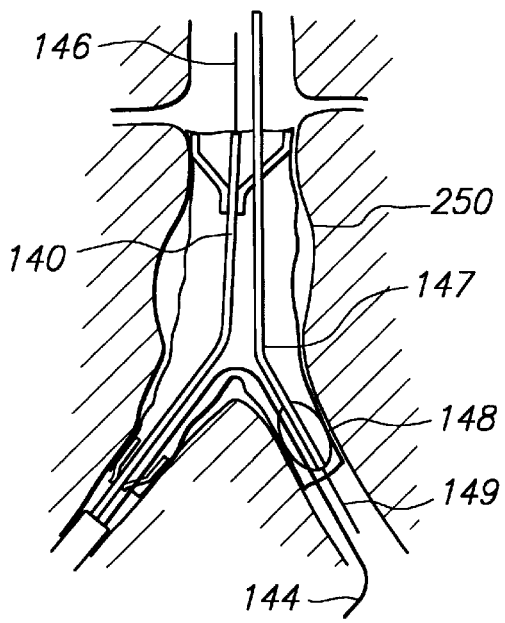

Referring now to FIGS. 9A–9C, an alternative method of deploying bifurcated graft 105 using some of the foregoing apparatus is described. In FIG. 9A, guide catheter 90 carrying guidewire 144 is shown inserted through the contralateral iliac artery while snare catheter 120 is shown inserted through the ipsilateral iliac artery. Guide catheter 90 is actuated to bend guidewire 144 into the ipsilateral iliac artery, where it is captured using snare catheter 120. Guidewire 144 is then pulled through the ipsilateral iliac artery so that it extends across the iliac bifurcation. Both guide catheter 90 and snare catheter 120 are withdrawn, leaving guidewire 144 in place (with suitable hemostatic valves, not shown, at either end).

In FIG. 9B, end 144a of guidewire 144 is connected to leg 105b of bifurcated graft 105, for example, by elongated suture 145, that extends outside the body when leg 105b is positioned in the contralateral iliac artery. Bifurcated graft 105 is disposed within introducer catheter 60 in a manner similar to that shown in FIG. 4A, except that introducer catheter 60 has been retracted slightly in the proximal direction to enable guidewire 144 to be coupled to suture 145. Graft 105 and graft delivery component 140 are then retracted within introducer catheter 60.

Graft 105, graft delivery component 140, and introduced catheter 60 are then advanced along guidewire 146, which has its distal end located in the proximal cuff of the aneurysm. As the graft is advanced along guidewire 146, leg 105b rides along guidewire 144 that spans the iliac bifurcation, so that leg 105b is pulled into the contralateral iliac artery as the graft is advanced distally along guidewire 146.

With respect to FIG. 9C, catheter 147 carrying inflatable balloon 148 is disposed in leg 105b of graft 105 along guidewire 149. As shown in FIG. 9C, guidewire 149 and catheter 147 are advanced from above, for example, through the brachial/carotid arteries, to push any wrinkles out of the graft material forming leg 105b. Balloon 148 is deflated once the graft has been pushed into position in the contralateral iliac artery, and then graft 105 is affixed using stents as described hereinabove. Guidewires 144, 146 and 149 and graft delivery component 140 (and introducer catheter 60) are then withdrawn.

It will therefore be seen that the method of FIGS. 9A–9C differs from that of FIGS. 8A–8C in that the guidewire used to locate leg 105b of the graft in the contralateral iliac artery is brought across the iliac bifurcation prior to insertion of graft 105 into the aorta. Consequently, in the method of FIGS. 9A–9C, the graft may be pulled into the contralateral iliac artery as graft 105 is deployed, rather than after leg 105a has been deployed. Furthermore, in accordance with the principles of the present invention, contralateral leg 105b of the graft is positioned using balloon 148 and catheter 147, which is inserted through graft 105 from above. In addition, graft 105 may be fully retrieved within introducer catheter 60 at any point up until a stent is deployed to fasten the graft in place.

Figure 10A:
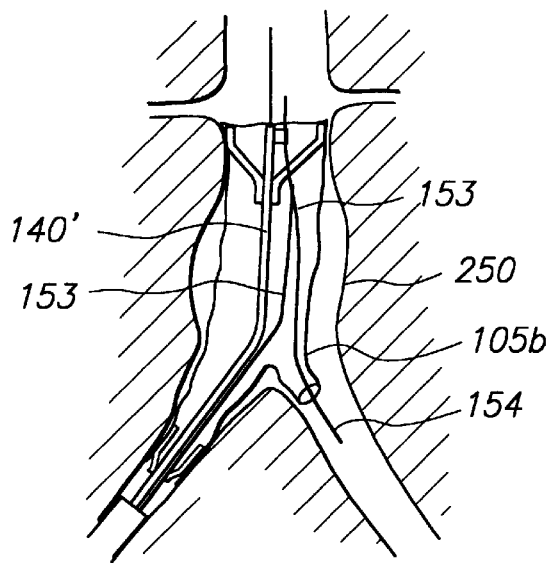
FIGS. 10A–10D are partial sectional views showing deployment of a bifurcated graft in accordance with a further alternative method of the present invention.
Figure 10B:
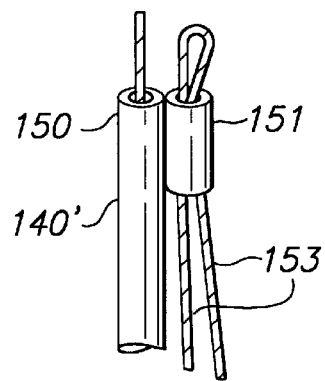

Referring now to FIGS. 10A–10D, a further method of deploying bifurcated graft 105 is described. In FIG. 10A, graft 105 is deployed using graft delivery component 140' similar to that of FIGS. 8 and 9, with the exception that graft delivery component 140' includes elastomeric sleeve 150 disposed near distal end 151. Sleeve 150 grips guidewire 153, which is threaded through leg 105b of graft 105, in a doubled-over manner, so that distal end 154 of guidewire 153 extends beyond the end of leg 105b. Accordingly, when graft 105 is deployed from introducer catheter 60, leg 105b and guidewire 153 are exposed within the aneurysm.

Figure 10C:
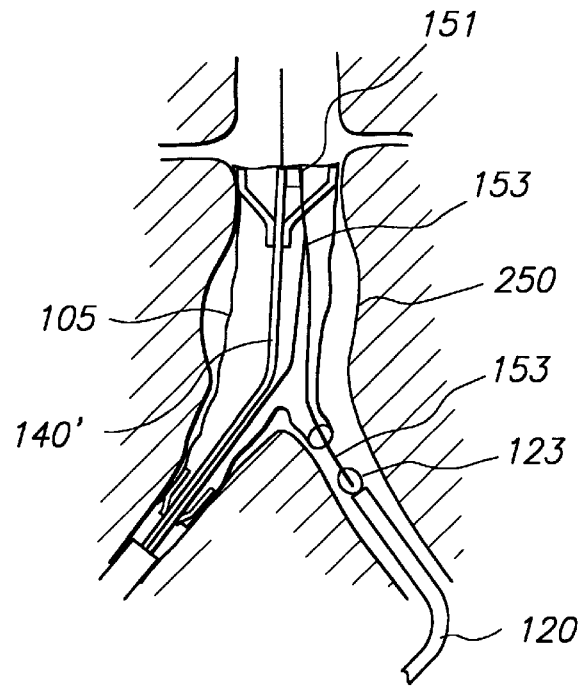
Figure 10D:
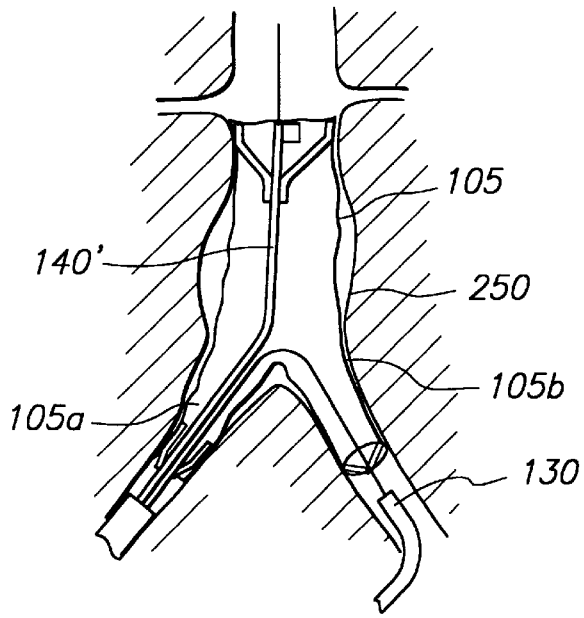

As seen in FIG. 10C, snare catheter 120 is inserted through the contralateral iliac artery so that snare 123 is positioned within the aneurysm. Snare catheter 120 is then manipulated to capture end 154 of guidewire 153 in snare loop 123. Snare loop 123 is then closed, and snare catheter 120 is withdrawn proximally. As snare catheter 120 is retracted, guidewire 153 breaks free of sleeve 151, thereby permitting the guidewire to be pulled through the contralateral iliac artery. As illustrated in FIG. 10C, when snare catheter 120 is withdrawn, guidewire 153 spans the iliac bifurcation. Positioning catheter 130 may next be advanced along guidewire 153 to engage leg 105b, and the remainder of the graft implantation is performed as described hereinabove with respect to FIGS. 8 and 9.

To facilitate removal of guidewire 153 from sleeve 151, the sleeve may include a vertical slit or tearable perforation. In this manner, guidewire 153 is held securely in place against inadvertent release, but may be removed by snare catheter 120 when desired. By comparison to the methods described above with respect to FIGS. 8 and 9, the method described with respect to FIG. 10 obviates the step of having to redirect the end of the guidewire used in leg 105b of the graft, since sleeve 153 holds the guidewire in an orientation directed towards the contralateral iliac artery. As will of course be understood with respect to all of the foregoing methods, visualization of the catheter bending and guidewire snaring steps are performed using suitable imaging techniques (e.g., fluoroscopy, CT or MRI scanning) with appropriate markers on the catheters to provide localization in the image.

As will be apparent to one of skill in the art, variations of the foregoing components may be designed. For example, stent delivery component 50 could be combined in series with graft delivery component 10 or 140, so that the stent is located proximally of the proximal group of fingers within the introducer catheter. In addition, the number and placement of the radially expandable fingers may be varied, for example, by providing a greater number of fingers, or by changing the circumferential or longitudinal spacing of the fingers.

Additionally, graft 100 and graft 105 also may have integrated longitudinally-oriented barbed support bars (not shown), as described in U.S. Pat. No. 4,617,932, to assist in fixing the graft to the walls of the aorta, or may include elastic fibers that assist the radially expandable fingers in opening the graft once introducer catheter 60 is retracted. Moreover, graft 105 may include pseudo-elastic alloy wires or hoops (e.g., formed of nickel-titanium alloy) that assist in opening the common lumen or legs of the graft.

The methods and apparatus of the present invention have been described with reference to excluding aneurysms occurring in the abdominal aorta, however, the methods and apparatus of the present invention are equally applicable to gastro-intestinal, respiratory, reproductive organ and urethral applications and elsewhere where is desirable to "reline" a hollow-body organ or vessel, and for repairing arterio-venous fistulas.

While preferred illustrative embodiments of the present invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A method of implanting a graft in a hollow-body organ or vessel, the method comprising steps of:

providing a graft, an introducer catheter and a graft delivery component having a plurality of fingers, each of the fingers including a retention wire that releasably engages the graft, the fingers and the graft retained in a contracted state by the introducer catheter;

inserting the graft delivery component and introducer catheter transluminally to deliver the graft to a desired position in the hollow-body organ or vessel; and retracting the introducer catheter to allow the fingers to resiliently deploy to an expanded state in which the graft is held in apposition to an interior wall of the hollow-body vessel or organ.

2. The method as defined in claim 1 further comprising steps of:

providing a stent delivery component for delivering a stent;

inserting the stent delivery component transluminally to a position adjacent the graft; and while retaining the graft in apposition to the interior wall of the hollow-body organ or vessel with the graft delivery component, deploying a first stent from the stent delivery component to affix a first end of the graft to the interior wall of the hollow-body organ or vessel.

3. The method as defined in claim 2 further comprising steps of:

while retaining the graft in apposition to the interior wall of the hollow-body organ or vessel with the graft delivery component, deploying a second stent from the stent delivery component to affix a second end of the graft to the interior wall of the hollow-body organ or vessel.

4. The method as defined in claim 1 further comprising a step of retracting the retention wires to release the graft from the graft delivery component.

5. The method as defined in claim 2 wherein the hollow-body organ is an abdominal aorta that communicates with first and second iliac arteries and a brachial/carotid artery, the step of inserting the graft delivery component and introducer catheter transluminally to deliver the graft comprising inserting the graft delivery component and introducer catheter through a first iliac artery, and the step of inserting the stent delivery component transluminally to a position adjacent the graft comprises inserting the stent delivery component through one of the arteries in a group consisting of the first iliac artery, the second iliac artery and the brachial/carotid artery.

6. The method as defined in claim 1 wherein the graft delivery component further comprises a support tube, the step of inserting the graft delivery component and introducer catheter transluminally to deliver the graft to a desired position further comprising a step of moving the support tube in proximal and distal directions to adjust positioning of the graft.

7. The method as defined in claim 1 further comprising a step, after the step of moving the graft to a desired position, of retracting the graft within the introducer catheter to retrieve the graft.

8. The method as defined in claim 2 wherein the stent delivery component comprises an outer sheath and a balloon member, the stent disposed in a contracted state within the outer sheath, the step of deploying a first stent from the stent delivery component further comprising steps of:

disposing the stent delivery component so that the first stent, when deployed, partially overlaps the first end of the graft;

while retaining the stent delivery component in a desired position, retracting the outer sheath to permit the first stent to be at least partially deployed; and inserting the balloon member within the first stent and inflating the balloon member to lock the first stent in place.

9. The method as defined in claim 1 wherein the hollow-body organ or vessel includes a bifurcation having first and second branches and the graft is a bifurcated graft having a common lumen and first and second legs, the common lumen and first leg of the graft engaged with the graft delivery component, the method further comprising, prior to the step of inserting the graft delivery component and introducer catheter transluminally, steps of:

providing a snare catheter and guide catheter carrying a guidewire;

inserting the guide catheter and guidewire transluminally into the hollow-body organ or vessel through the first branch, the guidewire extending from the guide catheter;

manipulating the guide catheter to direct an end of the guidewire toward the second branch;

transluminally inserting the snare catheter through the second branch;

capturing the end of the guidewire with the snare catheter;

pulling the end of the guidewire through the second branch, so that the guidewire spans a bifurcation between the first branch and the second branch; and coupling the guidewire to the second leg of the graft.

10. The method as defined in claim 1 wherein the hollow-body organ or vessel includes a bifurcation having first and second branches and the graft is a bifurcated graft having a common lumen and first and second legs, the common lumen and first leg of the graft engaged with the graft delivery component, the method further comprising, after the step of retracting the introducer catheter, steps of:

providing a snare catheter, a positioning catheter, and guide catheter carrying a guidewire;

inserting the guide catheter and guidewire through the introducer catheter, the first leg, and into the common lumen of the graft;

manipulating the guide catheter to direct an end of the guidewire through the second leg;

transluminally inserting the snare catheter through the second branch;

capturing the end of the guidewire with the snare catheter;

pulling the end of the guidewire through the second branch, so that the guidewire spans a bifurcation between the first branch and the second branch;

inserting the positioning catheter through the second branch along the guidewire; and manipulating the positioning catheter to engage and position the second leg of the graft in the second branch.

11. The method as defined in claim 1 wherein the hollow-body organ or vessel includes a bifurcation having first and second branches and the graft is a bifurcated graft having a common lumen and first and second legs, the common lumen and first leg of the graft engaged with the graft delivery component, the graft delivery component releasably holding a guidewire that extends into the second leg, the method further comprising, after the step of retracting the introducer catheter, steps of:

providing a snare catheter and a positioning catheter;

transluminally inserting the snare catheter through the second branch;

capturing the end of the guidewire with the snare catheter;

pulling the guidewire with the snare catheter to free the guidewire from the graft delivery component;

pulling the end of the guidewire through the second branch, so that the guidewire spans a bifurcation between the first branch and the second branch;

inserting the positioning catheter through the second branch along the guidewire; and manipulating the positioning catheter to engage and position the second leg of the graft in the second branch.

12. A graft delivery system for implanting a tubular graft in a hollow-body organ or vessel comprising:

a support tube having a circumference;

a plurality of resilient fingers disposed about the circumference of the support tube, each of the resilient fingers having a tip, the resilient fingers movable between a compressed state in which the resilient fingers are compressively stressed so that the tips are disposed adjacent to the support tube and a deployed state in which the resilient fingers are in an unstressed state and the tips are deployed radially outward from support tube, each of the resilient fingers including retention means for releasably engaging a tubular graft; and an introducer catheter having a passageway, the introducer catheter being movable from a first position in which the plurality of resilient fingers are disposed within the passageway so that the introducer catheter compresses the resilient fingers to the compressed state and a second position in which the introducer catheter is retracted so that the plurality of resilient fingers are in the deployed state.

13. The graft delivery system as defined in claim 12 wherein the plurality of resilient fingers are arranged in proximal and distal groups on the support tube.

14. The graft delivery system as defined in claim 13 wherein each of the proximal and distal groups comprises three resilient fingers.

15. The graft delivery system as defined in claim 12 wherein the plurality of resilient fingers are disposed equidistant apart around the circumference of the support tube.

16. The graft delivery system as defined in claim 12 wherein each of the resilient fingers includes a portion defining a lumen, the retention means comprising:

an aperture disposed in a lateral face of each finger adjacent the tip, the aperture communicating with the lumen; and a retention wire having a distal end, the retention wire disposed in the lumen and movable from a first position in which the distal end is disposed distally of the aperture and a second position in which the distal end is disposed proximally of the aperture, the retention wire releasably engaging a portion of the graft extending into the aperture in the first position.

17. The graft delivery system as defined in claim 16 further comprising means manipulable by a user to retract the retention wires to the second position.

18. The graft delivery system as defined in claim 12 wherein the graft is a bifurcated graft having a common lumen and first and second legs, the support tube further comprising means for releasably engaging a guidewire so that the guidewire passes through the first leg and into the common lumen, and extends into the second leg.

19. The graft delivery system as defined in claim 12 further comprising a guide catheter having a steerable distal end.

20. The graft delivery system as defined in claim 12 further comprising a snare catheter including a snare loop.

21. The graft delivery system as defined in claim 12 further comprising a positioning catheter, the positioning catheter comprising:

a support tube;

a plurality of resiliently outwardly expanding fingers; and a sheath slidably disposed on the support tube for moving the plurality of resiliently outwardly expanding fingers from a transit position to a deployed position.

22. A stent-graft delivery system comprising:

a graft delivery component including:

a plurality of resilient fingers, each of the resilient fingers having a tip, the resilient fingers movable between a compressed state in which the resilient fingers are compressively stressed so that the tips are disposed adjacent one another and a deployed state in which the resilient fingers are in an unstressed state and the tips are deployed radially outward from one another; each of the resilient fingers including retention means for releasably engaging a tubular graft; and an introducer catheter movable from a first position in which the plurality of resilient fingers are retained in the compressed state and a second position in which the introducer catheter is retracted so that the plurality of resilient fingers are in the deployed state; and a stent delivery component, the stent delivery component carrying a stent for affixing the graft to a wall of a hollow-body organ or vessel.

23. The stent-graft delivery system as defined in claim 22 wherein the plurality of resilient fingers are arranged in proximal and distal groups.

24. The stent-graft delivery system as defined in claim 23 wherein each of the proximal and distal groups comprises three resilient fingers spaced equidistant apart.

25. The stent-graft delivery system as defined in claim 22 wherein each one of the resilient fingers includes a portion defining a lumen, the retention means comprising:

an aperture disposed in a lateral face of each finger adjacent the tip, the aperture communicating with the lumen;

a retention wire having a distal end, the retention wire disposed in the lumen and movable from a first position in which the distal end is disposed distally of the aperture and a second position in which the distal end is disposed proximally of the aperture, the retention wire releasably engaging a portion of the graft extending into the aperture in the first position.

26. The stent-graft delivery system as defined in claim 22 wherein the stent delivery component comprises:

an outer sheath having a transit position for transluminal insertion and a retracted position;

a core member disposed within the outer sheath, the core member carrying a nose cone at a distal end and a retaining member disposed on the core member spaced apart from the nose cone, the core member configured to accept a stent in a contracted state between the nose cone and the retaining member, the outer sheath retaining the stent in the contracted state when in the transit position.

27. The stent-graft system as defined in claim 26 wherein the stent delivery component further comprises a balloon member, wherein the core member includes a lumen for inflating the balloon member.

28. The graft delivery system as defined in claim 22 wherein the graft is a bifurcated graft having a common lumen and first and second legs, the support tube further comprising:

means for releasably engaging a guidewire so that the guidewire passes through the first leg and into the common lumen, and extends into the second leg; and a snare catheter including a snare loop for engaging the guidewire extending into the second leg.

29. The graft delivery system as defined in claim 22 further comprising:

a guide catheter having a steerable distal end; and a snare catheter including a snare loop.

30. The graft delivery system as defined in claim 22 further comprising a positioning catheter, the positioning catheter comprising:

a support tube;

a plurality of resiliently outwardly expanding fingers; and a sheath slidably disposed on the support tube for moving the plurality of resiliently outwardly expanding fingers from a transit position to a deployed position.

* * * * *